United States Patent [19]

Grundei et al.

[11] 4,167,047

[45] Sep. 11, 1979

[54] SHANKS FOR KNEE-JOINT ENDOPROSTHESES

[76] Inventors: Hans Grundei, Hohlandstr. 56; Joachim Henssage, Trentsaal 7; Wolfram Thomas, Zwinglistr. 1; Gerhard Schutt, Lothringer Str. 39, all of D-2400 Lübeck, Fed. Rep. of Germany

[21] Appl. No.: 773,395

[22] Filed: Mar. 2, 1977

[30] Foreign Application Priority Data

Mar. 16, 1976 [DE] Fed. Rep. of Germany ....... 2610922

[51] Int. Cl.² ............................................... A61F 1/24
[52] U.S. Cl. ...................................... 3/1.911; 3/1.91; 128/92 C
[58] Field of Search ................................. 3/1.9–1.913; 128/92 C, 92 CA; 32/10 A

[56] References Cited

U.S. PATENT DOCUMENTS

| 3,628,248 | 12/1971 | Kroder et al. ...................... 3/1.9 X |
| 3,685,058 | 8/1972 | Tronzo .................................. 3/1.912 |
| 3,805,302 | 4/1974 | Mathys ................................. 3/1.91 |
| 3,846,846 | 11/1974 | Fischer ................................. 3/1.913 |
| 3,995,323 | 12/1976 | Shersher ............................. 3/1.9 X |

FOREIGN PATENT DOCUMENTS

| 1961531 | 9/1970 | Fed. Rep. of Germany ............... 3/1.9 |
| 2114287 | 9/1972 | Fed. Rep. of Germany ............ 3/1.911 |
| 2253338 | 5/1974 | Fed. Rep. of Germany ............... 3/1.9 |

OTHER PUBLICATIONS

Trapezoidal-28, Total Hip Prostheses, Zimmer (Catalog), Zimmer Mfg. Co., Warsaw, Ind., p. A14–1, Rev. 2, Sep. 1974, (received Mar. 27, 1975).

*Primary Examiner*—Ronald L. Frinks
*Attorney, Agent, or Firm*—Kinzer, Plyer, Dorn & McEachran

[57] ABSTRACT

This invention relates to shanks for knee joint endoprostheses which, on implantation, are inserted in a space prepared in the spongiose and marrow of the receiving bone. The invention consists in matching the external contour of the shank for at least a part of its length to the cross-section of the medullar cavity in a normal human bone receiving the shank.

5 Claims, 9 Drawing Figures

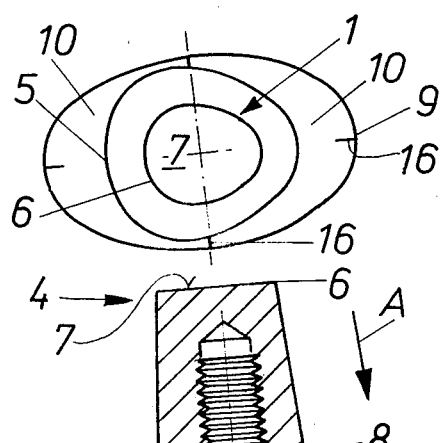
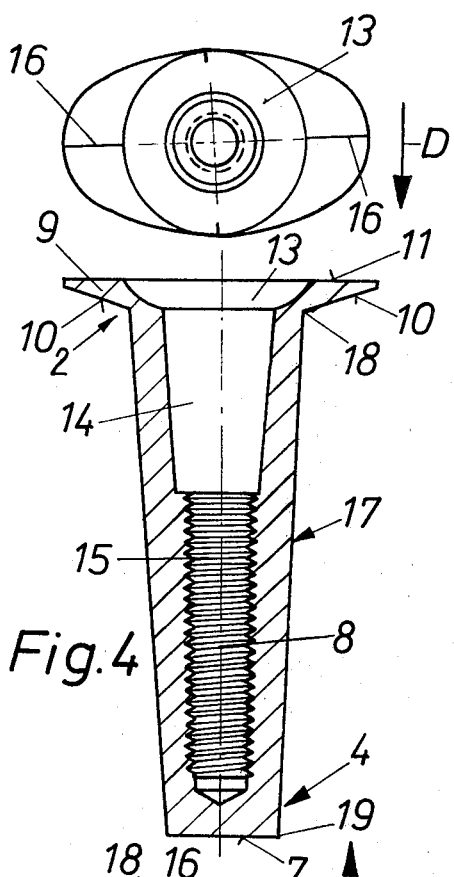

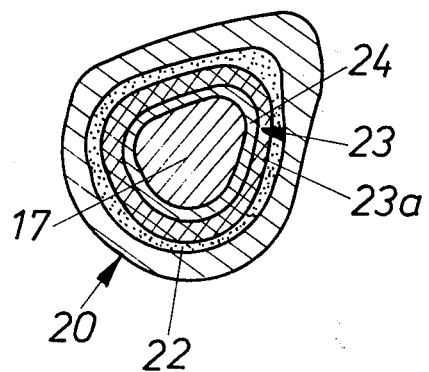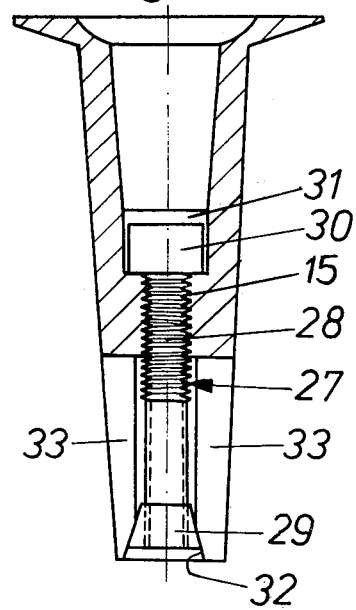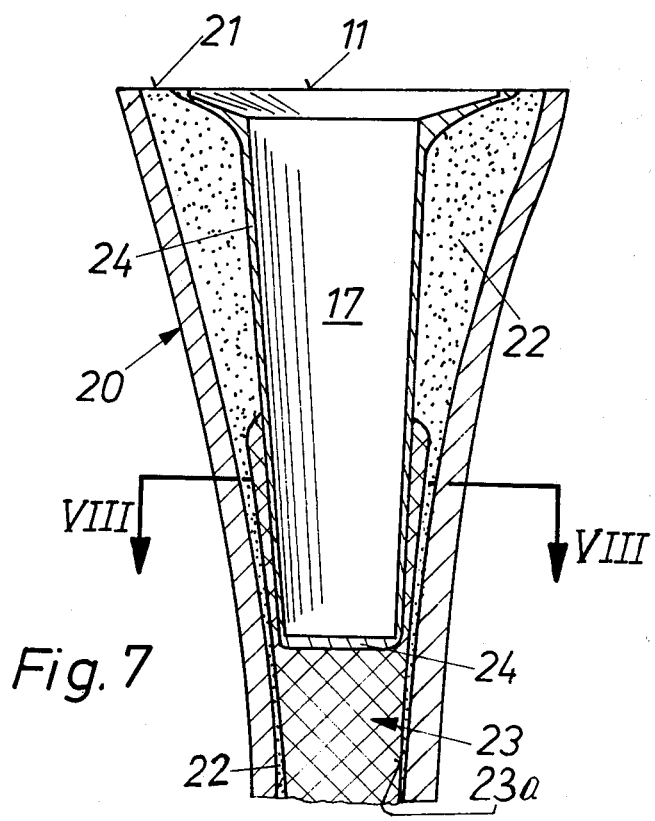

SHANKS FOR KNEE-JOINT ENDOPROSTHESES

BACKGROUND OF THE INVENTION

This invention relates to shanks for knee-joint endoprostheses of the kind which, when the prosthesis is being implanted, is inserted in a space prepared in the spongiose and marrow of the bone which is to receive the shank.

The shanks of known knee-joint endoprostheses are formed to be square or approximately square in cross-section with or without longitudinal flutes or splines, and they end in a more or less pronounced point. Their diameter is relatively small, being 8 to 10 mm for example, and is constant throughout their length and their length is 15 to 20 times the thickness of the shank. When prostheses having such shanks are implanted, the shanks reach a very long way into the medullar cavities in the thigh bone and shin bone of a human being. To ensure that the shanks are adequately anchored in the spongiose and in the medullar cavity, a cementing substance is used when the shanks are inserted.

The fact that the shanks of known knee-joint endoprostheses are relatively long and come to a point is a major disadvantage because they often damage the bone surrounding the medullar cavity when they are implanted, even though they are shaped into a curve to follow the slight curvature of the bone. Because of their slight curvature they cannot be inserted centrally into the bone, or can only be so inserted with difficulty, thus making it difficult to accurately position the endoprosthesis being implanted. Also, shaped shanks have the disadvantage that if prostheses are removed, the shanks can only be freed by damaging the end parts of the thigh and shin bones next to the knee joint; freeing them thus involves a loss of bone material. Also, shanks of square or approximately square cross-section do not provide adequate security against the implanted prosthesis turning, particularly during the phase of the operation when it is being cemented into place.

It is therefore an object of the invention to provide shanks, which can be implanted accurately in thigh and shin bones, for knee-joint endoprostheses in such a way as to be secure against turning, avoid damage to the bone, and are relatively simple to free again from the bone material.

This and other objects are achieved with shanks of the above mentioned kind, by matching the contour of the shank, which preferably tapers in the direction of its free end, for at least part of the length of the shank to the cross-section of the medullar cavity in a normal human bone which is to receive the shank.

Advantageously the shank is formed as a part separate from the remainder of the knee-joint endoprosthesis and, in its end portion nearer the knee-joint, is provided with a tapering axial bore to accept a conical spigot on the joint-part of the prosthesis. From the bottom of the tapering bore there extends an internally threaded axial hole in which an extracting tool can be engaged. The end of the shank nearer the joint has a flange-like collar with support faces.

A shank formed as above is relatively short and it is ensured that it can be centrally and non-rotatably inserted in the bone because its external contour in cross-section is matched to the cross-sectional shape of the medullar cavity in the thigh or shin bone. In addition, it allows damage to the bone to be avoided and can easily be freed from the bone since, in addition to being relatively short, it tapers, preferably uniformly, to its free end. The diameter of the shank is made sufficiently small at all points to provide a clearance between it and the remaining bone material, so that allowance can be made for individual differences between bones and so that adequate space is available for the cement used to anchor the shank.

The length of the steadily tapering section of the shank, which, in accordance with the invention, is of an anatomically matched shape, is advantageously 8 cm. This makes it possible to use only one type of shank since there is no need to make provision for individual differences in the thigh and shin bones. The principal used to anchor the shank is that of taper wedging. In principle the shank has a smooth surface, so that it can very easily be freed again by screwing a suitable tool into the aforementioned internally threaded hole in the shank and removing the shank by for example tapping the tool backwards. The basic cross-sectional shape of the shank according to the invention remains an important factor even when the shank is provided with support faces or other anchoring means to allow it to be anchored in the shaft of the bone without cement.

BRIEF SUMMARY OF THE DRAWINGS

In order that the invention may be more clearly understood, reference will now be made to the accompanying drawings which show certain embodiments thereof by way of example and in which:

FIG. 1 is an axial section through an embodiment of shank for a normal thigh bone, FIGS. 2 and 3 are end views along arrows A and B, FIG. 4 is an axial section through an embodiment of shank for a normal left shin-bone, FIGS. 5 and 6 are end views along arrows C and D, FIG. 7 shows a shank according to the invention implanted in a normal shin bone, FIG. 8 is a cross section on line VIII—VIII of FIG. 7, and FIG. 9 shows a further embodiment of shank according to the invention.

DETAILED DESCRIPTION OF PREFERRED EMBODIMENTS

FIGS. 1 and 2 show shanks according to the invention for a knee-joint endoprosthesis, the joint part of the prosthesis not being shown since it is not germane to the invention and thus taking any desired known form. In the present illustrative case the shanks are formed as items separate from the joint-part of the prosthesis but they could also be permanent parts of the joint section.

FIG. 1 shows a shank 1 which is to be inserted in the thigh bone and which is referred to as a femur shank. The femur shank shown tapers for its entire length between a point 3 at its end 2 adjacent the joint and its other end 4. The ratio of taper is preferably 1:10. The cross-sectional shape of the crank 1 is matched to the cross-sectional shape of the medullar cavity in the end of a normal thigh bone adjacent the joint, that it to say the external contour of the shank in cross-section substantially follows the internal outline of the walls of the medullar cavity in a normal thigh bone. In practice, this endows the femur shank with an anatomically conforming cross-section of oval shape, as is clearly shown by the outlines 5 and 6 in FIG. 2. The diameter of the external contour of the shank is however smaller than the corresponding diameter of the medullar cavity, i.e.

of the internal outline of the substantia corticalis of the bone, thus providing enough clearance between the shank and the bone material to allow for individual differences in bones and to provide space for anchoring cement.

Since the shank is at least sufficiently long for its end portion to project into the medullar cavity of a normal thigh bone, the proposed anatomically matched configuration of the shank-end 4 ensures that when the shank is inserted into the bone its implantation will be anatomically guided i.e. the shank can be inserted with an assurance that it is in correct angular position since the cross-section of its end matches the cross-sectional shape of the medullar cavity, allowing for the clearance mentioned. Because of the said clearance, the shank is able to turn to a certain extent in both directions, for which reason it is provided with an alignment mark.

At its end 4, the shank 1 has an end-face 7 which acts as a bearing surface and which extends perpendicularly or substantially perpendicularly to the longitudinal axis 8 of the shank. The end 2 of the shank nearer the joint has a flange-like collar 9 of oval outline (FIGS. 2 and 3) which has substantially crescent-shaped support faces 10. The collar can be satisfactorily embedded in the bone material and its support faces prevent the shank from sinking into the trabeculae of the thigh bone in an undesirable fashion during implantation. If the shank were to sink in during implantation there would be a risk of the shank, which is anchored on the principal of taper wedging, coming loose.

With respect to the flat end-face 11 at the end 2 of the shank nearer the joint, the longitudinal axis 8 of the shank 1, and thus the shank itself, is inclined. The angle of inclination α to the vertical 12 in FIG. 1 is preferably 5°. In this way the position of the axis of an implanted shank is matched to the natural angle of the thigh bone. FIG. 1 shows a femur shank for the left thigh bone.

At the joint end, the shank 1 is provided with a central recess 13 from which a tapering bore 14 extends approximately axially into the shank. As shown in FIG. 1, the centre axis of the tapering bore 14 preferably coincides with the vertical line 12 so that the conical spigot (not shown) on the joint-part of the prosthesis, which is wedged in the tapering bore to attach the joint-part, can be arranged on the joint-part so as to extend axially, which simplifies the manufacture of the join-part. Alternatively, however, the centre axis of the tapering bore may coincide with the longitudinal axis 8. From the bottom of the tapering bore 14 an internally threaded passage 15 penetrates further into the interior of the shank 1 and may if desired break through the end-face 7. The internally threaded passage is used as a positive engagement for a tool by means of which the shank can be removed from the bone when required. Advantageously, the line of the internally threaded passage follows the longitudinal axis 8 of the shank.

In addition, indexing means, e.g. in the form of marks or indentations 16 are made in the end-face 11 at end 2 of the shank and by aligning these with corresponding companion indexing means on the joint part of the prosthesis it can be ensured that the joint part is correctly aligned when fixed in the shank 1. The marks or indentations 16 may also be used to align the shank as explained above.

The second embodiment, shown in FIGS. 4, 5 and 6, has a shank 17 which is intended for insertion in a normal left shin-bone of a human being and is referred to as a tibia shank. In principle, it is of very much the same configuration as the femur shank 1 and the reference numerals used previously therefore apply to it also. The first difference from the shank 1 is that the cross-sectional shape of the shank 17 is not oval but, to match the internal outline of the wall of the medullar cavity in a normal shin-bone, is in the form of an irregular triangle with rounded corners and sides which curve outwards to a greater or lesser degree, as is clearly shown in FIG. 5. In the present case outlines 18 and 19 show the external contour of the tibia shank. This shank tapers steadily for example and in a straight line for its entire length, the ratio of taper used again being preferably 1:10.

Other differences are that, to suit the naturally upright position of a normal shin bone, the tibia shank is not inclined in relation to its end face 11 adjacent the joint. Also, the tapering bore 14 extends coaxially to the internally threaded hole 15.

It has been found that with a maximum shank diameter of approxiamtely 3 cm at 3 or 18 a shaft length of approximately 8 cm, not counting the collar 9, is adequate. As already mentioned, the shank 1 or 17, which consists for example of a standard steel for implantation use, preferably has a ratio of taper of 1:10. The maximum diameter of the oval collar 9 is approximately 5 cm and its minimum diameter approximately 3 cm. The preferred dimensions for the tapering bore are 16 mm for its diameter at the base with a depth of 27 mm. In this case too the ratio of taper is preferably 1:10.

FIG. 7 shows a tibia shank 17 cemented into a shin bone 20. The knee-joint end of the shin bone is first made flat by removing the joint face. Using a scooping-out tool and a template which is placed on the flat surface 21 so formed and which contains a hole matching the cross sectional shape required for the shank, a hollow is then created in the spongiose 22 and the medullar cavity 23 of the shin bone 20 and the walls of this are covered with a cementing substance 24, e.g. acrylic cement. The tibia shank 17 is then inserted into the hollow and pressed down so that its end face 11 at the end adjacent the joint lies flush with the aforementioned flat surface 21 of the shin bone 20. It can clearly be seen that adequate clearance for the cementing substance 24 is left between the shank 17 and the bone material.

The cross-sectional view in FIG. 8 clearly shows the anatomically conforming angular position of the implanted shank 17 relative to the internal outline of the walls 23a of the medullar cavity of the shin bone 20.

Although the external contour of the shank 1 or 17 is shown and has been described as tapering in a straight line, it may also take the form of a curved taper. Also, rather than being smooth and even, it may be provided with projections and/or depressions. As an example, known sawtoothed shaped ridges could be used, although in this case the crests of the ridges, which run circumferentially to the shank, would have the form of circumferential outline in cross-section called for by the invention. Alternatively or in addition, the shank may also be provided with a clamping arrangement which allows parts of the shank to be forced apart radially. Such an arrangement, 27, is shown in FIG. 9 for example. It consists of a screw 28 which is advantageously axially arranged in the internally threaded hole 15, and of a tapered pressure collet 29, against which the screw pulls in order to generate a clamping force which acts radially outwards. While the head 30 of the screw 28 is accommodated in a counter-bore 31 which continues from the inner end of the tapering bore 14 and leaves adequate clearance for the head 30, the tapered collet 29 engages in a tapering seating 32 at the free end 4 of the shank. At its free end 4, the shank is provided with axial slots 33 to allow it to yield radially.

As a further modification, the shank may be endowed with the cross-sectional shape according to the invention in only one section of its length or in a plurality of sections which are spaced apart from one another. The shank may also be formed as a telescopic shank, in which case it has at least two telescopic parts. In the course of implantation, the telescopic parts, whose cross-section is of the form according to the invention, are then forced into the bone in the axial direction, where they are able to set up a wedged connection to the bone, although they remain connected to one another.

If the external contour of the shank is specially formed to be other than smooth and/or if the shank is to be fixed into position in some way such as is indicated above, then cementing substances may be dispensed with since the special formations form supporting faces and the bone material as it regenerates itself, grows entirely around them and since it is possible to fix the shank accurately in the way explained.

Although the shank has been described as tapering to its free end 4 and is preferably used in this form, it is however conceivable, as an extreme case, for it to be of constant thickness throughout its length, in which case it is of course of the cross-sectional shape according to the invention as detailed above. The scope of the invention thus also extends to an external contour for the shank of this nature. The shank according to the invention for joint endoprostheses is thus shaped in cross-section to conform to the normal anatomy of the joint ends of the thigh and shin bones.

We claim:

1. In an elongated shank for knee-joint endoprosthesis which, when the prosthesis is implanted, is inserted in a space prepared in the spongiose and marrow of the medullar bone cavity to receive the shank which is to be cemented in the bone, the improvement consisting in that the cross-section of at least that length portion of the shank body which projects into the medullar cavity of said bone is anatomically matched substantially to the cross-sectional shape of the medullar cavity but is smaller in cross-section than the medullar cavity thereby to provide clearance to allow for individual bone differences, the end of the shank adjacent to the prosthesis having a flange-like collar with support faces on its surface adjacent to the shank body to axially limit insertion of the shank, said shank being substantially egg-shaped in outline corresponding to the medullar cavity of a leg bone, said shank body having a tapering axial bore at the end nearer the prosthesis and said bore having a widened end to receive the prosthesis, and an indexing means located on said collar with which a corresponding index means on the prosthesis can be brought into alignment.

2. A shank according to claim 1 wherein the collar is of oval outline with tapered support faces to be embedded in the bone.

3. A shank according to claim 1 wherein the surface of the collar opposite the support faces is flat, said shank body being on inclined axis compared to the plane of said flat surface.

4. A shank according to claim 2 wherein the surface of the collar opposite the support faces is flat, the axis of said shank being substantially perpendicular to the plane of said flat surface, and the cross section of said shank being substantially triangular with rounded corners substantially in the configuration of the medullar cavity of the shin bone.

5. A shank according to claim 3 in which the angle of inclination is about 85°.

* * * * *